United States Patent [19]

Trébillon

[11] 4,032,582
[45] June 28, 1977

[54] METHOD OF OBTAINING PRIMARY ALCOHOLS WITH STRAIGHT CHAINS FROM $C_4$ HYDROCARBON CUTS

[75] Inventor: Emile Trébillon, Neuilly-sur-Seine, France

[73] Assignee: Rhone-Poulenc Industries, Paris, France

[22] Filed: June 24, 1976

[21] Appl. No.: 699,339

[30] Foreign Application Priority Data

June 27, 1975 France .............................. 75.20253

[52] U.S. Cl. ............................ 260/632 D; 252/526; 252/532; 260/448 A; 260/459 R; 260/615 B
[51] Int. Cl.[2] .................... C07C 29/00; C07C 31/32
[58] Field of Search .................... 260/448 A, 632 D

[56] References Cited

UNITED STATES PATENTS

| | | | |
|---|---|---|---|
| 2,863,896 | 12/1958 | Johnson | 260/632 D |
| 2,889,385 | 6/1959 | Catterall et al. | 260/448 A |
| 3,014,941 | 12/1961 | Walsh | 260/448 A |
| 3,077,490 | 2/1963 | Fernald | 260/448 A |
| 3,347,894 | 10/1967 | Trebillon et al. | 260/448 A |

Primary Examiner—Joseph E. Evans
Attorney, Agent, or Firm—McDougall, Hersh & Scott

[57] ABSTRACT

A method of preparing primary alcohols, virtually all with a straight chain, in which the molecular proportions are distributed on both sides of a maximum centered at 8 to 16 carbon atoms.

It comprises: reaction between a $C_4$ hydrocarbon cut and activated aluminum and hydrogen, during which the concentration of dibutylaluminum monohydride in the reaction medium is adjusted between 20 and 80 molar %, to form a mixture of butylaluminum isomers; then a reaction wherein the isobutyl and secondary butyl groups contained in the mixture of isomers are displaced by the 1-butene in a $C_4$ hydrocarbon cut, in at least two reaction zones arranged in series and fed in counter-current flow with the said mixture of butylaluminum isomers and with the $C_4$ hydrocarbon cut; fixing ethylene on the tri-n-butylaluminum thus obtained to a chain length of $C_8$ to $C_{16}$; then oxidation with a gas containing oxygen and hydrolysis in a mixture of aliphatic primary alcohols. Such alcohols find use in detergent compositions after alkoxylation and/or sulphation of such mixtures of primary alcohol.

12 Claims, 3 Drawing Figures

METHOD OF OBTAINING PRIMARY ALCOHOLS WITH STRAIGHT CHAINS FROM C$_4$ HYDROCARBON CUTS

The invention relates to a method of obtaining primary alcohols with straight chains from C$_4$ hydrocarbon cuts without preliminary separation of the 2-butene, when present, and of the isobutene contained therein.

Triglycerides of natural origin, which are subsequently hydrogenated, have long been the chief source of straight-chain primary alcohols with an even number of carbon atoms.

However, the scarcity of natural fatty substances and consequently their high cost have encouraged the development of methods of synthesizing such alcohols, particularly from materials of petrochemical origin.

Thus, as a result of work done by Karl Ziegler, methods of synthesizing from ethylene and triethylaluminum have been used. They comprise the following stages:

- preparation of triethylaluminum, by reacting ethylene with aluminum and hydrogen in accordance with French Pat. No. 1,148,930;
- fixing ethylene on triethylaluminum by a so-called growth reaction, leading to alkylaluminums with a chain length statistically distributed around a maximum which may, if desired, be centered at 10 to 14 carbon atoms (French Pat. Nos. 1,066,167 and 1,273,795);
- oxidizing the alkylaluminums to alcoholates, with a gas containing oxygen, and hydrolyzing the alcoholates to a mixture of alcohols, which are separated according to their uses (French Pat. No. 1,134,907).

Another known method, described in the Ziegler et al French Pat. No. 1,134,878, makes use of triethylaluminum obtained in a so-called displacement reaction whereby the isobutyl radicals are displaced and isobutene is liberated from the triisobutylaluminum by ethylene. After the growth reaction with ethylene, oxidation and hydrolysis, as in the above program, straight-chain alcohols are obtained.

However, triisobutylaluminum cannot be used directly as the starting material for the chain-lengthening reaction with ethylene with a view to producing straight alcohols, since incorporation of the isobutyl radical in the chain leads to a branched structure (French Pat. No. 1,243,143).

Other straight alpha-olefins, such as 1-butene, may be used as raw materials to make up the trialkylaluminum which forms the starting material for the chain-lengthening reaction with ethylene. However, this implies the availability of alpha-olefins not containing any branched isomers or internal double bond, such as isobutene and 2-butene. Furthermore, these pure alpha-olefins are becoming more and more scarce because of the increasing demand for many chemical applications. This is a serious disadvantage.

The invention has for its object to remedy the above-mentioned disadvantages by using a raw material which is in plentiful supply and which has so far been in little demand, viz., C$_4$ hydrocarbon cuts obtained from various refining operations, such as cracking processes. The cuts may contain mixtures of isobutene, 1-butene, 2-butene and isobutane and do not require any preliminary separation of the 1-butene. This enables the upgrading of hydrocarbon cuts to be used in the production of essentially straight-chain fatty alcohols, thereby increasing the profitability of their manufacture, whereas at the present time the cuts are used as cheap industrial or domestic fuels. Another substantial advantage in using the C$_4$ hydrocarbon cuts is the ease in transporting them in a liquefied state, as compared with ethylene which requires high pressures or the construction of gas pipe lines.

Direct conversion of such cuts to butylaluminum under known operating conditions, i.e. in the presence of hydrogen and aluminum, e.g. at 80°–220° C and pressure of 20 to 250 bars, has so far produced a mixture of butylaluminum isomers which, in addition to the primary butyl radical, contain isobutyl and secondary butyl radicals, which are unsuitable for the preparation of straight-chain derivatives by subsequent fixation of ethylene.

The method of the invention, apart form enabling the 1-butene in the C$_4$ cut to be used, enables a large part of the 2-butene, when present, to be converted into normal tributylaluminum. This represents a more complete utilization of the C$_4$ raw material.

According to the invention, applicants have in fact perfected a method of preparing primary alcohols, virtually all with a straight chain, in which the molecular proportions are distributed on both sides of a maximum centered at 8 to 16 and preferably 10 to 14 carbon atoms, comprising the stages of preparing normal tributylaluminum, fixing ethylene on the butylaluminum to an average chain length of C$_8$ to C$_{16}$, then oxidizing with a gas containing oxygen and hydrolyzing in a mixture of aliphatic primary alcohols, characterized in that a C$_4$ hydrocarbon cut is reacted with activated aluminum and hydrogen, the cut containing 0 to 95% by weight of 1-butene, 0 to 75% by weight of 2-butene, with the proviso that the sum of 1-butene and 2-butene represents at least 15% by weight, 4 to 70% by weight of isobutene and 0 to 66% by weight of butane and isobutane, thus giving a mixed organic aluminum compound (also referred to hereinafter as mixed butylaluminum) essentially comprising a mixture of butylaluminums:

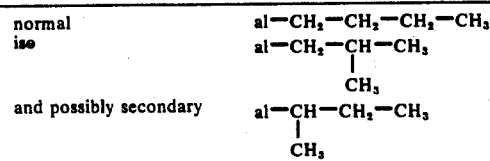

wherein al represents one-third gram-atom of aluminum in the combined state: that during this operation, the dibutylaluminum monohydride concentration present is adjusted between 20 and 80 molar %, and that the organic aluminum compound is then submitted to a reaction in which the isobutyl and possibly the secondary butyl groups are displaced by the 1-butene in a C$_4$ hydrocarbon cut comprising 15 to 95% by weight of 1-butene, 0 to 75% by weight of 2-butene, 4 to 75% by weight of isobutene and 0 to 66% by weight of butane and isobutane, in at least two reaction zones arranged in series and fed in countercurrent relationship with the said mixture of butylaluminum isomers, on the one hand, and with the C$_4$ hydrocarbon cut, on the other hand.

The number of displacement reaction zones may vary widely, depending on the technical solution adopted: an autoclave or a column with bubble trays, inter alia.

As an indication, the number may be 5, 10 or indeed up to 30 reaction zones and even more.

A previously described, the carbon raw materials which may be used in the present invention are C$_4$ hydrocarbon cuts obtained by cracking or any petrochemical operation, preferably after separation of the butadiene. Such separation is usually effected by extraction with selective solvents, and is generally applied to the whole production of C$_4$ hydrocarbons, because of the high value of butadiene. The admissible content of butadiene in the C$_4$ cuts used is preferably less than 0.5% by weight, because of the formation of polyfunctional organic aluminum compounds (organoaluminiques), i.e. containing double bonds and/or more than one atom of aluminum linked to one and the same molecule in the process applied. If the proportion of butadiene were to exceed this value, it would have to be eliminated by any known method, such as selective extraction, absorption in the form of copper complexes, reaction with maleic anhydride and preferably selective hydrogenation to butene.

It is also possible and in some cases advantageous to use C$_4$ cuts containing very little isobutene, e.g. from 4 to 10% by weight, such as the effluent from the manufacture of liquid polyisobutenes. In such manufacture, the whole C$_4$ cut is treated with a polymerizing agent, such as aluminum chloride. Part of the isobutene is retained, but generally at least 4% by weight of the hydrocarbon is left in the effluent gas.

Although the essential purpose of the invention is the direct use of crude butene-butane cuts, it would not be going beyond the scope of the invention to use cuts in which some constituents have been more or less completely removed by a chemical operation or physical separation (distillation or selective extraction inter alia).

The C$_4$ hydrocarbon cut used for the displacement reaction, in which the isobutyl groups are displaced, finally, has the following preferred composition by weight:

| | |
|---|---|
| 1-butene | 20 to 70% |
| 2-butene | 10 to 60% |
| isobutene | 4 to 50% |
| butane + isobutane | 3 to 40% |
| butadiene | 0.01 to 0.2% | with a 1-butene/isobutene weight ratio of 0.4 to 17/1.

The mixed butylaluminum, formed from a C$_4$ hydrocarbon cut as defined above, from active aluminum and from hydrogen, preferably at from 120° to 200° C and at a pressure of 80 to 150 bars, essentially comprises: normal butylaluminum derived directly from 1-butene and indirectly from 2-butene, either after isomerization of 2-butene to 1-butene or by isomerization of secondary to normal butylaluminum; secondary butylaluminum derived directly from 2-butene; and isobutylaluminum derived from isobutene.

The butylaluminums may be of the tributylaluminum Al (C$_4$H$_9$)$_3$ type and/or of the dibutylaluminum monohydride Al H (C$_4$H$_9$)$_2$ type.

The active aluminum, i.e. the aluminum with the protective surface layer of oxide and/or sulphide removed from it, is obtained by any known method, e.g. by a chemical method according to French Pat. No. 1,313,863, by introducing a dialkylaluminate of an alkali metal in the reaction medium, or by a physical method, such as mechanical abrasion. The reagents are brought into contact by mechanically agitating the mass or, better still, by circulating the gas phase, enabling good contact to be established between the three phases present, gas, liquid and solid.

The mixed butylaluminum may be formed in any type of reactor known for that purpose, but it is particularly advantageous to use the type of arrangement described in the patent application of Masotti et al, filed concurrently herewith and entitled "Method and Arrangement for Preparing Alkylaluminums". In this arrangement, the liquid phase in the reactor is drawn off in a decanting zone specially adapted to the reactor proper.

In order to avoid parasitic reactions of isomeration of 1-butene to 2-butene, hydrogenation of butenes and fixation of butenes on the butylaluminums to give branched octylaluminums, it is essential to the method of the invention that the dibutylaluminum monohydride concentration in the organic aluminum compound present in the reactor should be kept at an optimum value of from 20 to 80 molar % and preferably within the range of 30 to 65 molar %.

Below the lower limit of 20% of monohydride in the organic aluminum compound, the parasitic reactions tend to develop rapidly, whereas above 80% the productivity of this phase of the process diminishes considerably.

The proportion of monohydride, determined by frequent samplings of reactive liquid phase, is thus kept within the range defined above by increasing flow rate of the C$_4$ cut if the concentration of monohydride tends to increase and by reducing it if the opposite happens. The value stipulated for this concentration increases with the proportion of 1-butene in the C$_4$ cut and with a rise in the reaction temperature.

Thus with a C$_4$ cut containing 40 to 70% of 1-butene and operating at a temperature of from 140° to 160° C, the proportion of monohydride should preferably be adjusted to from 50 to 65 molar %. With the same cut but operating between 120 and 140° C, the proportion should preferably be adjusted between 30 and 50 molar %.

For a C$_4$ cut containing 20 to 60% of 2-butene and less than 10% of 1-butene, and operating at a temperature of from 150° to 190° C, the proportion of monohydride should be adjusted to a value preferably from 50 to 60 molar %.

Another feature of the invention is that the mixed organic aluminum compound, obtained in the manner just described, then undergoes a reaction in which the isobutyl and secondary butyl groups are displaced by the 1-butene in a C$_4$ cut, in at least two reaction zones arranged in series and fed in countercurrent flow with the mixture of butylaluminum isomers, on the one hand, and with a C$_4$ cut, on the other hand.

Applicants have in fact made the unexpected finding that substantially pure normal tributylaluminum, i.e. tributylaluminum of over 95% by weight purity and preferably at least 97% by weight purity, can be obtained in this way from C$_4$ hydrocarbon cuts containing non-negligible proportions, even large proportions, of isobutene and most often 2-butene.

It is appropriate, according to the invention, for the temperature in the set of displacement reaction zones to be from 120° to 180° C and preferably from 130° to 160° C.

In a special embodiment, the temperature of the last reaction zone, before the outlet for the normal tributylaluminum, is lowered to a value between 80° and 110° C, so as to promote conversion of the resulting dibutylaluminum monohydride to tributylaluminum.

The balance of the reaction:

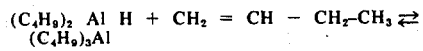

is in fact displaced to the right at a relatively low temperature, but the reaction rates are acceptable only from 80° C.

Pressure in the set of displacement reaction zones, according to the invention, is from 1 to 50 bars absolute and preferably from 2 to 20 bars absolute. The effect of overpressure, obtained by injecting compressed $C_4$ cut, is to promote solubility of the butenes in the liquid phase containing chiefly of butylaluminum(s) and consequently to increase the productivity of the process according to the invention. The pressure in the last reaction zone, before the outlet for the normal tributylaluminum, may be lower than that in the other reaction zones.

The average residence time of the liquid phase of butylaluminum in the set of displacement reaction zones depends on temperature, pressure and the composition of the $C_4$ cut used. As an indication, the time is generally from 0.1 to 30 hours and most often from 0.2 to 3 hours.

In one embodiment of the invention, the stage where the mixture of butylaluminums is formed and the stage where the isobutyl and secondary butyl groups are displaced are fed directly with fresh $C_4$ cuts, which may be identical or different from one another. At the stage where the mixed butylaluminum is formed, the 1-butene and/or part of the 2-butene are converted to normal butylaluminum, while another part of the 2-butene is converted to secondary butylaluminum.

In the displacement stage, on the other hand, the 2-butene returned to the free state from the combined form — secondary butylaluminum — is not used, and only the 1-butene is used to form normal butylaluminum.

In another embodiment of the invention, only the displacement stage is supplied with a fresh $C_4$ cut, while the state where the mixture of butyl aluminums (mixed butylaluminums) is formed is fed from the $C_4$ effluent, with the 1-butene virtually exhausted, resulting from the displacement reaction stage. In order to avoid accumulation of isobutene in the circuit, in cases where the $C_4$ cuts are rich in that isomer, it may be necessary to interpolate a distillation stage as a preliminary means of separating part of the isobutene before the $C_4$ cut, in which the 1-butene is exhausted, is passed to the stage for the formation of mixed butylaluminums. In this synthesis of butylaluminums, the 2-butene is largely converted to normal butylaluminum. The secondary butylaluminum, which forms simultaneously and in a smaller quantity from the 2-butene, is displaced to the following stage and liberates 2-butene, which is recycled and used to prepare mixed butylaluminum together with the stream of $C_4$ cut in which the 1-butene is exhausted.

On leaving the last displacement zone, the normal tributylaluminum according to the invention is submited to a growth reaction with ethylene by a known method, as described e.g. in French Pat. Nos. 1,066,167 and 1,273,795 in the name of Karl Ziegler. The reaction is carried out at a pressure of from 30 to 300 bars, the most favorable range being from 100 to 200 bars. The rate of the reaction is governed chiefly by the temperature. High temperatures are desirable, provided that the apparatus used enables the heat reaction to be dissipated, since they enable fast reactions to be obtained. The range of appropriate temperatures is from 80° to 200° C. Below 110° C, the reaction will take several hours, whereas suitable reaction rates are obtained from 120° C to 170° C in tubular reactors, which are easy to construct and where heating conditions may easily be controlled.

The following phase in the process comprises oxidizing the straight-chain alkylaluminums resulting from the preceding stage, by means of a gas containing oxygen, such as air or any other mixture of oxygen with an inert gas. Pure oxygen may equally be used.

Since the reaction is very vigorous, until about half the theoretical oxygen has been fixed, the oxygen must be added to the reaction medium fairly moderately to begin with, by limiting its partial pressure or by diluting the gaseous phase with an inert gas, such as nitrogen. Since the fixing of the second half of the oxygen is less vigorous, it is advantageous to increase the concentration of oxygen gradually, and the partial pressure of oxygen may be brought to about 10 bars absolute.

It is advantageous to carry out oxidation in the inert solvent, such as an aliphatic or aromatic hydrocarbon and, more particularly, in a mixture of $C_4$ aliphatic hydrocarbons, as described in French Pat. No. 1,315,743.

In an embodiment suitable for complete oxidation of the trialkylaluminums to alcoholates, the method described in French Pat. No. 1,389,504 is applied. In this method, oxidation is finished in the presence of small quantities of an alkylaluminum in which the degree of oxidation is less than the average degree of oxidation of the reaction material.

The temperature range which may be employed for the oxidation reaction is from −10° to 140° C and preferably from 20° to 60° C.

Hydrolysis of the alcoholate to straight-chain primary alcohol is carried out with a reagent containing water by any known method. By operating in a substantially neutral, stongly acid or strongly alkaline medium, alumina, aluminum salts or alkali metal aluminates may be obtained as a by-product, as the case may be.

The invention covers mixtures of primary alcohols, almost all with a straight chain, in which the molecular proportions are distributed on both sides of a maximum centered at 8 to 16 and preferably 10 to 14 carbon atoms, characterized in that they may contain from 0.01 to 4% of molecules with a chain branched by the methyl groups and/or that they have the properties of those obtained by the process described above. It also covers the distillation products of these mixtures of primary alcohols.

The invention also covers the uses of these essentially straight-chain primary alcohols, and more particularly the uses in the fields of detergents, plasticizers and additives for oils and cosmetics.

In the uses as detergents, a distillation cut may be taken from the mixture of primary alcohols according to the invention, containing e.g. alcohols with 10 to 18 carbon atoms and with an average of 14 carbon atoms. These may undergo alkoxylation and more particularly polyethoxylation by any known method, and the resultant product may be incorporated in detergent formulations in the usual way. These alcohols also lend themselves very readily to obtaining sulphates and corresponding ethoxysulphates for use in liquid or solid detergent compositions, shampoos and other surfactant compositions.

In the preparation of alkylethoxylates (alcoylethoxylates) the condensate generally contains from 5 to 50 recurring ethoxy units and, in the case of its subsequent sulphation, and condensate generally contains an average of 1 to 5 recurring ethoxy units.

Surfactants prepared from the primary alcohols, according to the invention, may be associated with one or more types of constituents selected from: other known non-ionic, anionic, cationic and zwitterionic surfactants; builders such as phosphates and/or polyphosphates, silicates and sequestering agents; bleaching agents such as per salts, inorganic and/or organic peroxides; anti-redeposition agents such as derivatives of cellulose (carboxymethylcellulose) or synthetic organic polymers such as polyacrylates, soluble polyesters and polyvinylpyrrolidone; enzymes; optical brighteners, dyes and perfumes.

Typical detergent compositions are obtained from the following general formulation:

| | |
|---|---|
| surfactants containing 2 to 100% by weight of surfactant prepared from the primary alcohols of the invention, per 98 to 0% by weight of one or more known non-ionic, cationic, anionic or zwitterionic surfactants such as alkylbenzene-sulphonates, ethoxylated alkylphenols and alkylbetaines | 5-30 |
| alkali metal perborate | 0-30 |
| alkali metal tripolyphosphate | 0-80 |
| enzymes | 0-5 |
| alkali metal and/or alkaline earth metal silicates | 0-20 |
| carboxymethylcellulose | 0-5 |

In uses as plasticizers, the primary alcohols of the invention are esterified generally by mono or polyfunctional acids, e.g. phthalic acid or anhydride, to give dialkylphthalates.

As far as uses as additives for lubricating oils are concerned, it is a question of using organic polymers which will be resistant to shearing and have a good viscosity index. These are often polyacrylates of primary alcohols, according to the invention.

As a further explanation of the method of the invention, the description which follows refers to the three accompanying drawings, in which.

Figure 1:
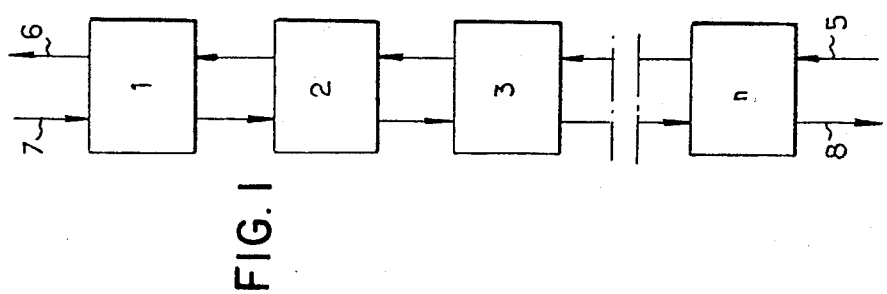
FIG. 1 is a flow diagram showing a certain number of displacement reactors 1, 2, 3 ... up to n (n may e.g. be equal to 10); there are arranged in series and agitating means (not shown) are provided in them to aid contact between gas and liquid.

In FIG. 1, the butylaluminums circulate from inlet 7 to outlet 8 between the reactors in the order 1, 2, 3 . . . n, while the $C_4$ hydrocarbons circulate from inlet 5 to outlet 6 in the opposite order n . . . 3, 2, 1. The mixture of butylaluminum isomers, entering reactor 1, thus meets a gas containing very little 1-butene and a relatively great deal of isobutene and 2-butene. Conversely the butylaluminum in the last reactor n meets the fresh $C_4$ cut with the maximum content of 1-butene.

The set of displacement reactors may, in practice, take the form of a series of separate autoclaves equipped with mechanical agitators, between which the gases are circulated by over-pressure at the inlet to the last reactor n, and where the liquids are transferred from one reactor to another in counter-current to the flow of gases, by means of pumps.

Figure 3:
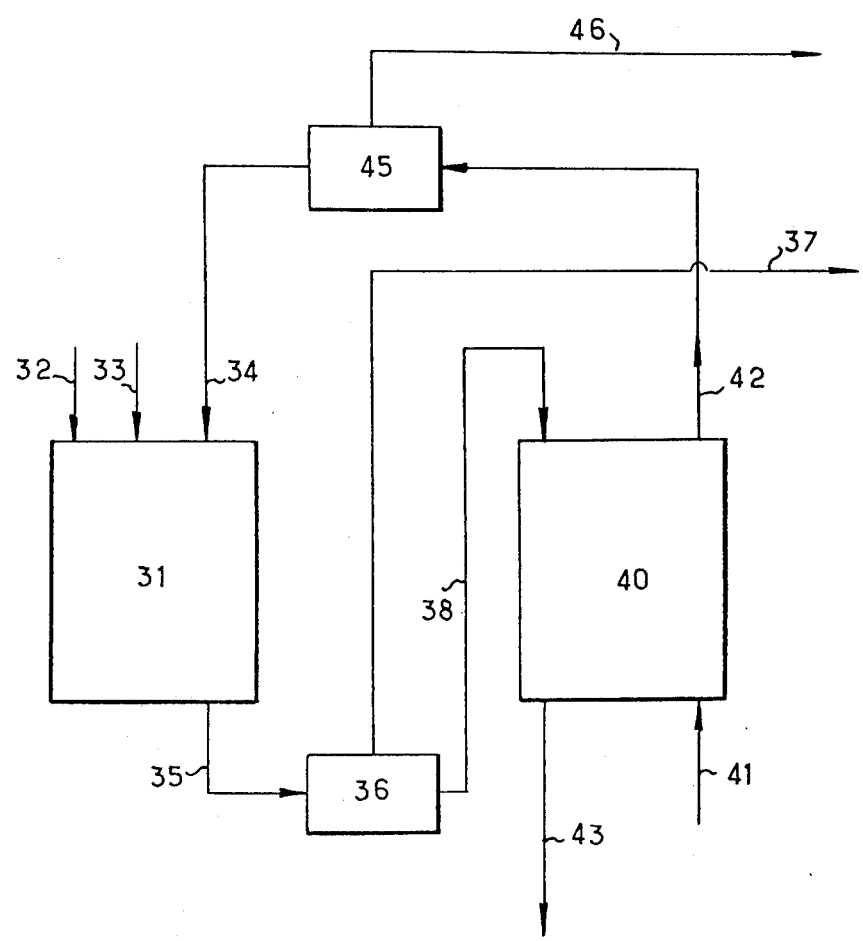
FIG. 3 is a flow diagram showing a different embodiment of the stage at which the mixed butylaluminums are formed and the displacement stage, which also leads to normal tributylaluminum.

In a different form of apparatus which may be used, gas-liquid contact in each autoclave is obtained by admitting the gas at the bottom by means of tubes and/or perforated diffuser plates, not shown in FIGS. 1 and 3.

Figure 2:
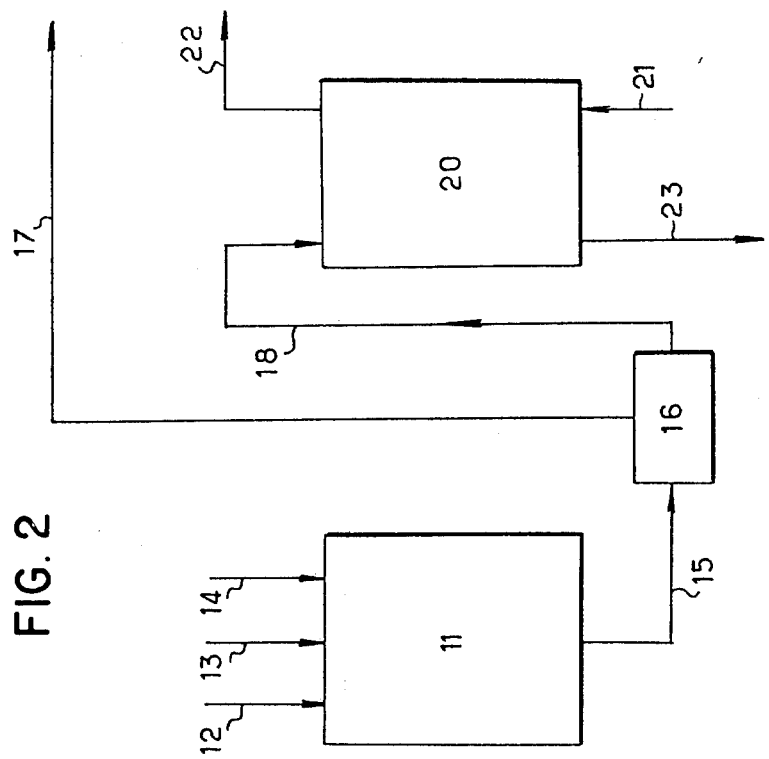
FIG. 2 is a flow diagram showing an embodiment of the stage at which the mixed butylaluminums are formed and the displacement stage leading to normal tributylaluminum.

Other possible embodiments of displacement reactors, which are equally not shown in FIGS. 1 to 3, include a bubble cap column of the type holding back a large amount of liquid, in which the liquid is circulated by gravity.

In FIG. 2, the reactor 11 for making the mixed butylaluminum, which is a mixture of butylaluminum isomers in the form of tributylaluminums and monohydride of dibutylaluminums, is supplied continuously with hydrogen 12, activated aluminum 13 and $C_4$ hydrocarbons 14. The mixed butylaluminum and $C_4$ hydrocarbons enriched with saturated compounds are drawn off continuously at 15. These hydrocarbons are separated in the distillation means 16 in the form of a cut 17 rich in butane and isobutane, while the mixed butylaluminum 18 is passed into the system of displacement reactors 20.

In the system of displacement reactors, the mixed butylaluminum reacts with a $C_4$ hydrocarbon cut injected counter-currently at 21. This gives, on the one hand, an effluent 22 of $C_4$ hydrocarbons in which the 1-butene is exhausted and, on the other hand, normal tributylaluminum 23.

In FIG. 3, the reactor 31 for making the mixed butylaluminum, is fed continuously with hydrogen 32, activated aluminum 33 and $C_4$ hydrocarbons 34 rich in 2-butene, resulting from the system of displacement reactors 40 via a distillation column 45. The mixed butylaluminum and $C_4$ hydrocarbons enriched with saturated compounds are drawn off continuously at 35.

These hydrocarbons are separated from the mixed butylaluminum in the distillation means 36, in the form of a cut 37 rich in butane and isobutane, while the mixed butylaluminum 38 is passed into the system of displacement reactors 40.

In the system of displacement reactors, the mixed butylaluminum reacts with a $C_4$ hydrocarbon cut which is injected in counter-current flow at 41 to give, on the one hand, a normal tributylaluminum 43 and, on the other hand, an effluent 42 of $C_4$ hydrocarbons in which the 1-butene is exhausted. This effluent contains a considerable proportion of 2-butene, much of which is converted to normal butylaluminum by being recycled to the reactor 31 for synthesizing the mixed butylaluminum. But to avoid an accumulation of isobutene in the circuit, the stream of hydrocarbons 42 passes into a distillation column 45, where a fraction 46 rich in isobutene is eliminated at the top and a fraction 34 rich in 2-butene is eliminated at the bottom and recycled to reactor 31.

The non-restrictive examples which follow are given solely to illustrate the invention. Unless otherwise stated, the quantities and percentages given in them are expressed by weight.

EXAMPLE 1

Using the schematical lay-out shown in FIG. 2, an organic aluminum compound is prepared, essentially comprising a mixture of butylaluminum isomers. This is done in reactor 11, in which activated aluminum, supplied at 13, is reacted with hydrogen, supplied at 12 and a hydrocarbon cut, supplied at 14 and obtained from petroleum cracking. The cut has the following composition:

1-butene : 53.9%; 2-butene : 28.6%; isobutene : 7.2%; butane : 8.7%; isobutene : 1.5%; butadiene : 0.05%.

The reaction is carried out at 140° C at a pressure of 120 bars in a steel reactor. A suitable form of agitation enables contact to be maintained between the three phases, represented essentially by solid aluminum, liquid butylaluminum and gaseous hydrogen.

The proportions of reagents continuously injected per hour into the reactor for synthesizing the butylaluminums are as follows:
aluminum : 104 parts; hydrogen : 13 parts; $C_4$ cut : 656 parts;

The rate at which the reagents are introduced is controlled so that the molecular proportion of dibutylaluminum monohydride (which can be measured by complexometry with isoquinoline) is maintained at 56% in the mixed butylaluminum of effluent 18.

At the outlet from the reactor a mixture of $C_4$ hydrocarbons and mixed butylaluminum is collected at 15. The mixture is separated at 16 to give 635 parts of mixed butylaluminum at 18 and 136 parts of $C_4$ hydrocarbons of the following composition at 17:

1-butene : 4.4%; 2-butene : 15.5%; isobutene : 2.9%; butene + isobutene : 77.2%.

The mixed butylaluminum, comprising 81% of normal butyl radicals, 11% of secondary butyl radicals and 8% of isobutyl radicals, is passed into the system of displacement reactors 20 after the unreacted solid impurities have been filtered off.

The system of reactors, shown in attached FIG. 1 with $(n) = 4$, comprises, a series of four indentical steel autoclaves. Each of them is equipped with an internal mechanical agitator provided to ensure good contact between the gas and liquid phases. The temperature is kept at the desired value by circulating hot oil within the double walls of the autoclaves: 150° C in autoclaves 1, 2 and 3 and 100° in autoclave 4.

The gases are circulated by over-pressure at the inlet to autoclave 4 and emrge from reactor 1 through an expansion valve at 6, after having reacted successively in autoclaves 4, 3, 2 and 1. An hourly flow of 460 parts of $C_4$ cut is thus injected at 5 into reactor 4 at a pressure of 10 bars absolute; the cut is of the following composition:

1-butene : 53.9%; 2-butene : 28.6%; isobutene : 7.2%; butane : 8.7%; isobutane : 1.5%; butadiene : 0.05%.

The losses of pressure due to circulation of the gases are small enough for the pressure in autoclave 1 to be at least 9 bars absolute.

The $C_4$ hydrocarbons recovered at outlet 6, at an hourly rate of 339 parts, are of the following composition:

1-butene : 7.7%; 2-butene : 59.9%; isobutene : 18.6%; butene + isobutane : 13.9%.

The mixed butylaluminum, injected continuously at 7 into autoclave 1 by means of a volumetric pump at an hourly rate of 635 parts, is transferred by feed-regulated pumps successively to autoclaves 2, 3 and 4, where it reacts with the $C_4$ cut.

The liquid in reactor 4, containing substantially pure normal tributylaluminum, is drawn off at 8 at an hourly rate of 756 parts.

Its composition is as follows:
normal butylaluminum : 97.4%; isobutylaluminum : 1.5%; higher alkylaluminums, consisting largely of 2-ethyl hexyl aluminum : 1.1%. 99% of the molecules consist of trialkylaluminum and 1% monohydride of dialkylaluminum.

The average residence time of the butylaluminum in each of the autoclaves is 20 minutes, or 80 minutes for the whole system of displacement reactors.

The normal tributylaluminum, obtained in the displacement reaction, is then submitted to a chain-lengthening reaction, by reacting it with ethylene at a pressure of 130 bars, in a tubular reactor which is kept at 140° C by circulating oil in an external double jacket.

When the excess ethylene has expanded at atmospheric pressure, 2,150 parts of an alkylaluminum are obtained with an average chain length corresponding to 11.4 carbon atoms.

The alkylaluminum is dissolved in 2,150 parts of anhydrous toluene and submitted to oxidation with an air stream at a temperature of 40° C, at atmospheric pressure.

After hydrolysis with an aqueous solution of 10% sulphuric acid and separation of the water and hydrocarbons, 1,830 parts (yield : 88% of theory) of a mixture of alcohols are obtained. Their distribution as a function of the chain length is as follows:

$C_4$ : 1%; $C_6$ : 5%; $C_8$ : 12%; $C_{10}$ : 18%; $C_{12}$ : 20%; $C_{14}$ : 17%; $C_{16}$ : 12%; $C_{18}$ : 7%; $C_{20}$ and above : 8%.

These alcohols comprise 98.5% of normal primary alcohols.

First comparative test

As in example 1, a $C_4$ cut of the composition given in that example is reacted with activated aluminum and hydrogen. An identical apparatus is used, under the same conditions of temperature and pressure, but the rates at which the ragents are introduced are adjusted so that the molecular properties of dialkylaluminum monohydride in the mixed butylaluminum drawn off from the reactor is kept at 15 molar % instead of 56%.

The proportions of reagents continuously injected into the reactor per hour are as follows:
aluminum : 112 parts; hydrogen : 26 parts; $C_4$ cut : 1,196 parts.

At the outlet from the reactor, after expansion, 500 parts of $C_4$ cut of the following composition are collected:

1-butene : 0.8%; 2-butene : 2.4%; isobutene : 0.6%; butane + isobutane : 96.2%.

The mixed butylaluminum obtained, 832 parts, comprises 70% of normal butyl radicals, 9% of secondary butyl radicals, 8% of isobutyl radicals and 13% of branched $C_8$ radicals, essentially 2-ethyl hexyl.

By comparison with example 1, the drop in the content of monohydride is found to have led, firstly, to less good utilization of the $C_4$ hydrocarbons, since the total yield from the conversion of butene and isobutene has passed from 88% in example 1 to 58% in the present test. Secondly, the formation of alkylaluminum with the branched $C_8$ radicals, less than 1% at this state in example 1, has passed to 13%.

The impure mixed butylaluminum is passed into the system of displacement reactors, as in example 1, with 360 parts of fresh $C_4$ cut of the composition already stated. 380 parts of an effluent are collected, containing:

3.8% of 1-butene; 51.9% of 2-butene; 22% of isobutene; 10.4% of butene and isobutane; 11.9% of branched $C_8$ hydrocarbons, essentially 2-ethyl 1-hexene.

846 parts of crude normal tributylaluminum of the following composition are also obtained:

normal butylaluminum : 93.1%; isobutylaluminum : 0.7%; branched octylaluminums, essentially 2-ethyl hexylaluminum : 6.2%.

The tributylaluminum is too strongly contaminated by compounds with a branched chain, 6.9% altogether, to be used in preparing straight-chain alcohols by the method of the invention. If the conversions are continued as in example 1, a mixture of alcohols is finally obtained comprising 5.8% of molecules with a branched chain. This makes them useless for normal applications of fatty alcohols of natural origin, such as the preparation of biodegradable detergents.

Second comparative test

The activated aluminum, hydrogen and a $C_4$ cut are reacted under conditions identical to those in example 1, except that the rate at which the reagents are introduced is adjusted so that the molecular concentration of dialkylaluminum monohydride in the mixed butylaluminum drawn off is kept at 85%.

The process of forming mixed butylaluminum is found to slow down very considerably, dropping from 771 parts under the conditions in example 1 to 191 parts. Such a reduction in productivity is a very serious disadvantage to industrial exploitation of the process.

EXAMPLE 2

Using the schematic lay-out in FIG. 3 of the accompanying drawings, an organic aluminum compound is first prepared, essentially comprising a mixture of butylaluminum isomers. This is done in reactor 31, which is fed with activated aluminum at 33, with hydrogen at 32 and with a recycled $C_4$ hydrocarbon cut at 34; the cut comes from the system of displacement reactors 40 by way of a distillation column 45 which will be described below in this same example. The composition of the $C_4$ cut is as follows:

1-butene : 2.3%; 2-butene : 51.7%; isobutene : 39.7%; butane + isobutane : 6.5%.

The reaction is carried out at 170° C and a pressure of 120 bars in a steel reactor 31 similar to that used in example 1. The proportions of reagents fed continuously into the reactor per hour are as follows: - aluminum activator: 25% solution of sodium dibutylaluminate prepared from the mixed butylaluminum drawn off from the same reactor : 12 parts; aluminum : 93 parts; hydrogen : 13 parts; $C_4$ cut : 614 parts.

The rate at which the reagents are introduced is adjusted so that the molecular proportion of dibutylaluminum monohydride in the organic aluminum compound obtained is 60%.

At the outlet from the reactor, a mixture of $C_4$ hydrocarbons and mixed butylaluminum is collected at 35. It is separated at 36 to give 565 parts of mixed butylaluminum at 38 and 154 parts of $C_4$ hydrocarbons of the following composition at 37:

2-butene : 22.7%; isobutene : 15.6%; butane and isobutene : 61.7%.

The mixed butylaluminum, containing 431% of normal butyl radicals, 12% of secondary butyl radicals and 45% of isobutyl radicals, is passed into the system of displacement reactors 40. This comprises a series of 5 autoclaves (not shown in FIG. 3) operating under the same conditions of temperature and pressure as in example 1.

The system of displacement reactors is fed at 41 with an hourly flow rate of 1,000 parts of a $C_4$ hydrocarbon and containing:

1-butene : 39.9%; 2-butene : 26.0%; isobutene : 26.0% butane + isobutane : 8%; butadiene : 0.1%.

The normal tributylaluminum production is drawn off continuously from the system of reactors at 43: 668 parts, containing 97.5% of normal butylaluminum, 1.3% of isobutylaluminum and 1.1% of alkylaluminums with chains of more than 4 carbon atoms. 99% of the molecules consist of trialkyluminums and 1% of monohydride of dialkylaluminums.

897 parts of a $C_4$ in which the 1-butene is exhausted are also drawn off from the system of displacement reactors at 42. The cut is of the following composition:

1-butene : 2.8%; 2-butene : 37.0%; isobutene : 51.3%; butane and isobutane : 8.9%.

The cut is passed into a distilling column 45 with trays of the bubble type, operating at a pressure of 9 bars absolute and an average temperature of 70° C. 283 parts of a $C_4$ cut, enriched with isobutene, are separated at the top of the column. The cut contains:

3.9% of 1-butene; 5.7% of 2-butene; 76.3% of isobutene; 14.3% of butane and isobutane.

614 parts of a $C_4$ cut enriched with 2-butene and of the composition already indicated at the beginning of this example are obtained at the bottom of the distilling column 34 and recycled to the reactor for synthesizing the mixed butylaluminum.

As in example 1, the normal tributylaluminum obtained at the outlet 43 of the system of displacement reactors is successively submitted to a chain-lengthening reaction with ethylene, oxidation and hydrolysis. This gives a mixture of straight-chain alcohols of substantially the same composition as the mixture of alcohols in example 1.

EXAMPLE 3

This example illustrates the application of the mixture of primary alcohols, according to the invention, in the detergent field.

The following detergent composition is prepared: - mixture of primary $C_{10}$ to $C_{16}$ alcohols centered at $C_{12}$ and obtained by the method of the invention, then condensed with

| | |
|---|---|
| 9 moles of ethylene oxide by a known method | 10% |
| sodium tripolyphosphate | 44% |
| sodium disilicate ($Na_2O . 2SiO_2$) | 6% |
| sodium perborate ($NaBO_3 . 4H_2O$) | 15% |
| sodium sulphate | 25% |

Pieces (12 × 12 cm) of polyester-cotton fabric (65-35), made for this type of test by Test Fabrics Inc. (U.S.A.) are impregnated with Spangler stain, prepared by the method described in Journal of American Oil Chemistry Society 1965, 42, pages 723–727. The pieces are washed in a liquor containing 8 g/liter of the above detergent composition, in a "Terg-O-tometer" (U.S. Testing Co.) at 60° C, with agitation at 85 revs/minute for 10 minutes. Two rinses are then given, lasting 2 minutes each.

The elimination of the stains is found to be very effective compared with the samples of stained fabric before washing.

I claim:

1. A method of preparing primary alcohols virtually all with a straight chain in which the molecular proportions are distributed on both sides of a medium centered at 8 to 16 carbon atoms, comprising the stages in sequence of preparing tri-n-butylaluminum, fixing ethylene on the butylaluminum to an average chain length of $C_8$ to $C_{16}$, oxidizing with a gas containing oxygen, and hydrolyzing in a mixture of aliphatic primary alcohols, characterized in that a $C_4$ hydrocarbon cut is reacted with activated aluminum and hydrogen at a temperature within the range of 80°–220° C and at a pressure within the range of 20–250 bars, the cut containing 0 to 95% by weight of 1-butene, 0 to 75% by weight of 2-butene, with the proviso that the sum of 1-butene and 2-butene represents at least 15% by weight, 4 to 75% by weight of isobutene and 0 to 66% by weight of butene and isobutene, thus giving a mixed organic aluminum compound essentially comprising a mixture of butylaluminums:

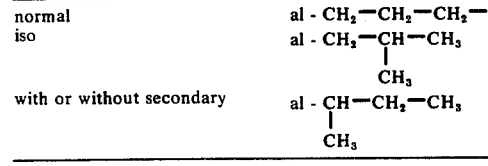

wherin al represents one-third gram-atom of aluminum in the combined state, the dibutylaluminum monohydride concentration present in the organic aluminum compound of the reaction medium being adjusted during this operation to between 20 and 80 l molar %, the organic aluminum compound is then submitted to a reaction in which the isobutyl and secondary butyl groups which may be present are displaced by reaction at a temperature within the range of 80°–180° C and a pressure within the range of 1–50 bars absolute by the butene in a $C_4$ hydrocarbon cut comprising 15 to 95% by weight of 1-butene, 0 to 75% by weight of 2-butene, 4 to 70% by weight of isobutene and 0 to 66% by weight of butane and isobutane, in at least two reaction zones arranged in series and fed in counter-current flow with the said mixture of butylaluminum isomers on the one hand and with the $C_4$ hydrocarbon cut, on the other hand.

2. The method as claimed in claim 1 in which the molecular proportions are distributed on both sides of a maximum centered at 10 to 14 carbon atoms.

3. The method as claimed in claim 1, characterized in that the $C_4$ hydrocarbon cut used for the displacement reaction contains from:
   20 to 70% by weight of 1-butene
   10 to 60% by weight of 2-butene
   4 to 50% by weight of isobutene
   3 to 40% by weight of butane and isobutane and 0.01 and 0.2% by weight of butadiene with a 1-butene/isobutene weight ratio of 0.4 to 17/1.

4. The method as claimed in claim 1 in which the concentration of dibutylaluminum monohydride in the organic aluminum compound of the reaction medium is kept at an optimum value within the range from 30 to 65 molar.

5. The method as claimed in claim 1 in which the temperature in the displacement reaction zones is from 120° to 180° C.

6. The method as claimed in claim 1 in which the temperature of the last reaction zone is lowered to a value between 80° and 110° C.

7. The method as claimed in claim 1 in which the pressure in all the displacement reaction zones is from 2 to 20 bars absolute.

8. The method as claimed in claim 1 in which the average residence time of the liquid phase of butylaluminum in all the displacement reaction zones is from 0.1 to 30 hours.

9. The method as claimed in claim 1 in which the average residence time of the liquid phase of butylaluminum in all the displacement reaction zones is from 0.2 to 3 hours.

10. The method as claimed in claim 1 in which the stage at which the mixture of butylaluminums is formed and the stage at which the isobutyl and secondary butyl groups are displaced are fed directly with fresh $C_4$ cuts which may be identical or different from one another.

11. The method as claimed in claim 1 in which only the displacement state is fed with a fresh $C_4$ cut, while the stage at which the mixed butylaluminum is formed is fed from the $C_4$ effluent substantially free from 1-butene, the 1-butene having been exhausted in the displacement reaction stage.

12. The method as claimed in claim 11 in which a distillation stage is interpolated for the preliminary separation of part of the isobutene, before the $C_4$ cut in which the 1-butene has been exhausted is passed to the stage where the mixed butylaluminums are formed.

* * * * *

UNITED STATES PATENT OFFICE
CERTIFICATE OF CORRECTION

Patent No. 4,032,582    Dated June 28, 1977

Inventor(s) Emile Trebillon

It is certified that error appears in the above-identified patent and that said Letters Patent are hereby corrected as shown below:

column 4, line 44, change "101%" to -- 10% -- column 10, line 48, change "ragents" to -- reagents -- column 13, at end of line 36, add "$CH_3$"

column 13, line 43 change "wherin" to -- wherein --

Signed and Sealed this

Twentieth Day of September 1977

[SEAL]

Attest:

RUTH C. MASON
Attesting Officer

LUTRELLE F. PARKER
Acting Commissioner of Patents and Trademarks